(12) United States Patent
Kurokawa

(10) Patent No.: US 8,970,212 B2
(45) Date of Patent: Mar. 3, 2015

(54) EDDY CURRENT PROBE

(71) Applicant: Mitsubishi Heavy Industries, Ltd., Tokyo (JP)

(72) Inventor: Masaaki Kurokawa, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 179 days.

(21) Appl. No.: 13/625,057

(22) Filed: Sep. 24, 2012

(65) Prior Publication Data

US 2013/0076349 A1 Mar. 28, 2013

(30) Foreign Application Priority Data

Sep. 27, 2011 (JP) ................. 2011-210125

(51) Int. Cl.
*G01R 33/12* (2006.01)
*G01N 27/90* (2006.01)

(52) U.S. Cl.
CPC ............ *G01N 27/90* (2013.01); *G01N 27/9013* (2013.01); *G01N 27/9033* (2013.01)
USPC .......................................... 324/240; 324/239

(58) Field of Classification Search
USPC .......................................................... 324/240
See application file for complete search history.

(56) References Cited

U.S. PATENT DOCUMENTS

| | | | |
|---|---|---|---|
| 2,964,699 A | 12/1960 | Perriam et al. | |
| 3,952,315 A | 4/1976 | Cecco | |
| 4,789,827 A | 12/1988 | Bergander | |
| 6,734,668 B2 * | 5/2004 | Hils et al. | 324/232 |
| 2009/0139335 A1 | 6/2009 | Kroning et al. | |
| 2010/0148767 A1* | 6/2010 | Hyodo et al. | 324/238 |

FOREIGN PATENT DOCUMENTS

| | | |
|---|---|---|
| JP | 36-020442 B2 | 10/1961 |
| JP | 55-101044 A | 8/1980 |
| JP | 57-70451 A | 4/1982 |
| JP | 57070451 A * | 4/1982 |
| JP | 61-032619 B2 | 7/1986 |
| JP | 63-133054 A | 6/1988 |
| JP | 06-094682 A | 4/1994 |
| JP | 2005-055325 A | 3/2005 |
| JP | 2008-309573 A | 12/2008 |

OTHER PUBLICATIONS

Extended European Search Report dated Jan. 30, 2013, issued in corresponding European Patent Application No. 12185764.3 (6 pages).

* cited by examiner

*Primary Examiner* — Bot Ledynh
(74) *Attorney, Agent, or Firm* — Westerman, Hattori, Daniels & Adrian LLP

(57) ABSTRACT

An eddy current probe 1 in accordance with the present invention has a structure in which a cross coil 7 is placed in a predetermined direction relative to permanent magnets 3 and 5 in the following manner. When the probe 1 is erected, the coil 7 is placed between the magnets 3 and 5 so that a direction CD in which the opposing portion 9a (9c) of the first coil 9 is extended intersects with a direction MD in which the magnets 3 and 5 are extended. In the same manner, when the probe 1 is erected, the coil 7 is placed between the magnets 3 and 5 so that a direction CD in which the opposing portion 11a (11c) of the second coil 11 is extended intersects with the direction MD in which the magnets 3 and 5 are extended.

4 Claims, 7 Drawing Sheets

Area with strong magnetic field

Area with variations in permeability

EDDY CURRENT PROBE

BACKGROUND OF THE INVENTION

1. Field of the Invention

The present invention relates to a probe for use in an eddy current testing.

2. Description of the Related Art

As a non-destructive testing method for detecting defects in metals, an eddy current testing (ECT) has been known. In the eddy current testing, a magnetic flux generated by an ECT coil to which an excitation current is applied generates an eddy current in a member to be measured, and a detection signal representing the magnetic flux generated by the eddy current is obtained as an output signal of the ECT coil. The detection signal thus obtained represents a position, shape, depth, or the like of a defect (flaw) of the test object. As such, the flaw detection is performed based on the detection signal.

However, in a case where the test object is a magnetic material, or in a case where the test object contains a magnetic material in an area under test, local variations in permeability are caused mainly due to variations in the material and, as a result, noise contained in the detection signal is increased and thereby lowering defect detection precision.

Against the lowered detection precision due to noise caused by variations in permeability, a countermeasure is proposed (for example, Japanese Patent Application Laid-Open No. 2008-309573) in which whether the detection signal is derived from a flaw of the test object or from noise is determined, and another countermeasure is proposed (for example, Japanese Patent Application No. 2005-55325) in which a permanent magnet for magnetic saturation is provided to the ECT coil so as to eliminate the influence from the variations in permeability.

Although detection precision for detecting a defect has been improved by former proposals, there is sometimes a failure in detecting a minute defect. In order to further improve the detection precision, it is particularly desired to prevent an eddy current probe that primarily performs flaw detection from picking up noise.

In view of these technical problems, the present invention has been made, and its object is to provide an eddy current probe that can further reduce noise presumably caused by permeability.

SUMMARY OF THE INVENTION

The inventors of the present invention have examined a noise reduction method by using a cross coil that is considered to be superior in detection performance for a defect that is orthogonal to or in parallel with a scanning direction as the ETC coil, as well as by using an eddy current probe provided with a permanent magnet for eliminating the influence from the variations in permeability. As a result, the inventors have found that noise can be remarkably reduced by using the eddy current probe in which the direction of an electric current flowing through the excited cross coil and the direction of a magnetic field generated by the permanent magnet intersect with each other.

The eddy current probe of the present invention, based upon this finding, is characterized by including a permanent magnet that generates a magnetic field in a predetermined direction and a cross coil placed in the magnetic field generated by the permanent magnet, and in this structure, the direction of an electric current flowing through the excited cross coil and the direction of the magnetic field generated by the permanent magnet intersect with each other.

In the eddy current probe of the present invention, the direction of the electric current and the direction of the magnetic field preferably intersect with each other with an angle in a range from 30 to 60°, more preferably, with an angle in a range from 40 to 50°, most preferably, with an angle of 45°.

In the eddy current probe of the present invention, a pair of permanent magnets, each having a rectangular parallelepiped shape, may be used as the permanent magnet, or a cylindrical permanent magnet may be used as the permanent magnet. In a case where the pair of rectangular parallelepiped permanent magnets are used, a cross coil may be placed between the pair of permanent magnets. Further, in a case where the cylindrical permanent magnet is used, the cross coil may be placed in a hollow portion of the permanent magnet. However, the present invention does not exclude the use of a permanent magnet having another mode.

In accordance with the present invention, it is possible to provide an eddy current probe that can further reduce noise presumably caused by permeability.

DETAILED DESCRIPTION OF THE PREFERRED EMBODIMENTS

The following description will discuss the present invention in detail based upon embodiments illustrated by accompanying drawings.

Figure 1A:
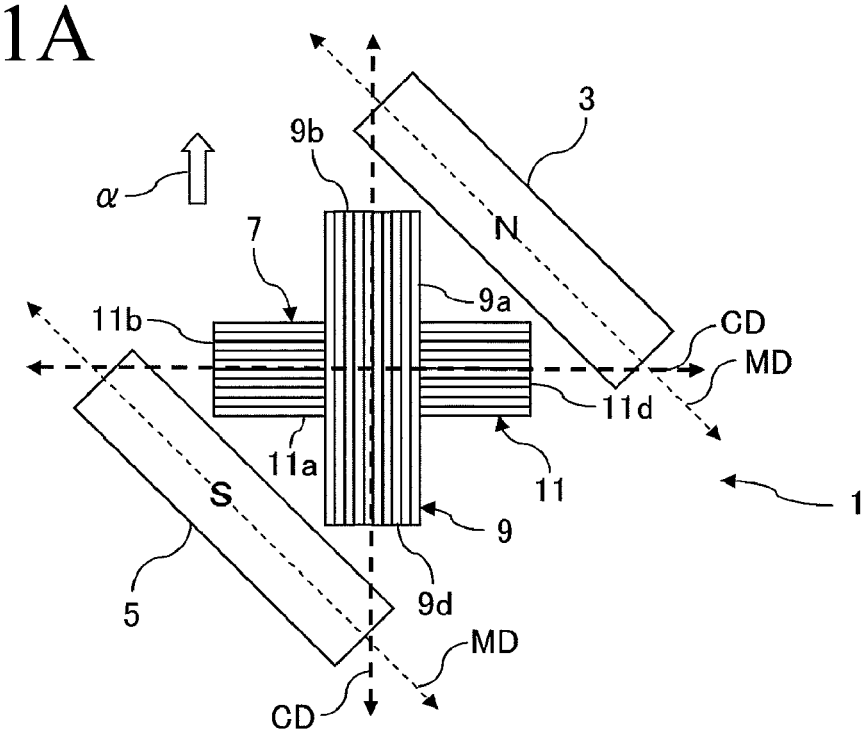
FIGS. 1A and 1B illustrate an eddy current probe in accordance with the present embodiment, FIG. 1A being a plan view and FIG. 1B being a front view.
Figure 1B:
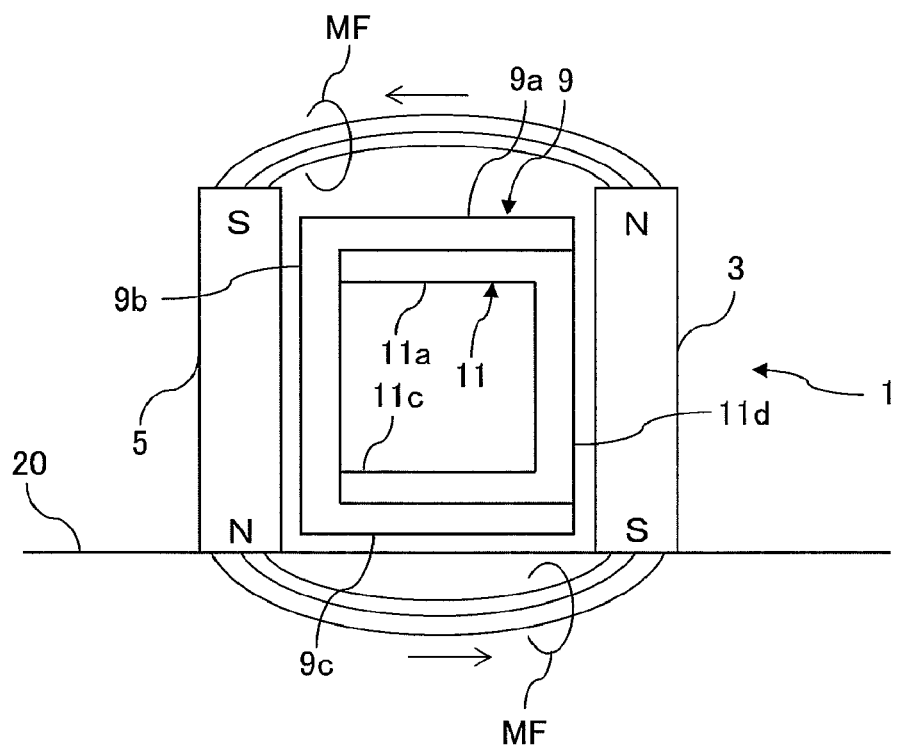

As shown in FIGS. 1A and 1B, an eddy current probe 1 (hereinafter, simply referred to as "probe") of the present embodiment is provided with a pair of permanent magnets 3 and 5 placed with a distance from each other and a cross coil 7 placed between the permanent magnets 3 and 5. The eddy current defect testing process is explained by exemplifying a structure in which the probe 1 is placed so as to make the permanent magnets 3 and 5 perpendicular to a test object 20 and a scanning is performed in a direction indicated by an arrow α. The layout in which the probe 1 is placed with respect to the test object 20 in this manner is referred to as "the probe 1 being erected".

In each of the plate-shaped permanent magnets 3 and 5, one end portion is magnetized to the N pole and the other end portion is magnetized to the S pole. The N pole of the permanent magnet 3 and the S pole of the permanent magnet 5, as well as the S pole of the permanent magnet 3 and the N pole of the permanent magnet 5, are placed to face with each other. Thus, as shown in FIG. 1B, a magnetic flux MF is formed so as to be directed from the permanent magnet 3 toward the permanent magnet 5, and another magnet flux MF is formed so as to be directed from the permanent magnet 5 toward the permanent magnet 3. In order to eliminate influence from variations in permeability generated in a defect detecting portion, the magnetic flux MF is exerted on the test object 20. In the case of FIGS. 1A and 1B, the magnetic flux MF, generated on the lower side of the permanent magnets 3 and 5, that is, on the side that is opposed to the test object 20, acts on the test object 20. It is to be noted that an Nd—Fe—B-system permanent magnet having high magnetic characteristics is preferably used as the permanent magnets 3 and 5.

The cross coil 7 is a differential coil of a self induction type, and is provided with a first coil 9 and a second coil 11 that are respectively longitudinal rectangular coils. However, this coil mode is merely one example, and an elliptical shaped (including a circle) coil may be used. The first coil 9 and the second coil 11 are respectively wound around so as to be made orthogonal to each other. In the exemplified structure, the entire first coil 9 is placed outside of the second coil 11. However, the entire first coil 9 may be placed inside of the second coil 11 or the first coil 9 and the second coil 11 may be alternately stacked layer by layer.

The first coil 9 is provided with opposing portions 9a and 9c that oppose to the test object 20 in parallel with each other at the time of scanning and upright portions 9b and 9d that rise perpendicularly to the test object 20 at the time of scanning. In the same manner, the second coil 11 is provided with opposing portions 11a and 11c that oppose the test object 20 in parallel with each other at the time of scanning and upright portions 11b and 11d that are made orthogonal to the test object 20 at the time of scanning.

In the self induction type cross coil 7, the first coil 9 and second coil 11 performs excitation as well as detection. The cross coil 7 is designed so as to output a difference (differential signal between the respective detection coils) between detection signals of the respective detection coils. The cross coil 7 is characterized in that in a case where magnetic noise is generated by a magnetic material portion contained in the test object 20, the influence of the magnetic noise can be easily cancelled by confirming a difference between the first coil 9 and the second coil 11. Since the cross coil 7 can in principle detect a defect without generating noise caused by liftoff, it is possible to detect the defect with high reliability.

The probe 1 is characterized in that the cross coil 7 is placed in a predetermined direction relative to the permanent magnets 3 and 5, as will be described below. That is, when the probe 1 is erected, the cross coil 7 is placed between the permanent magnets 3 and 5 in such a manner that a direction CD in which the opposing portion 9a (9c) of the first coil 9 is extended intersects with a direction MD in which the permanent magnets 3 and 5 are extended. In the same manner, when the probe 1 is erected, the cross coil 7 is placed between the permanent magnets 3 and 5 in such a manner that a direction CD in which the opposing portion 11a (11c) of the second coil 11 is extended intersects with the direction MD in which the permanent magnets 3 and 5 are extended.

Figure 2:
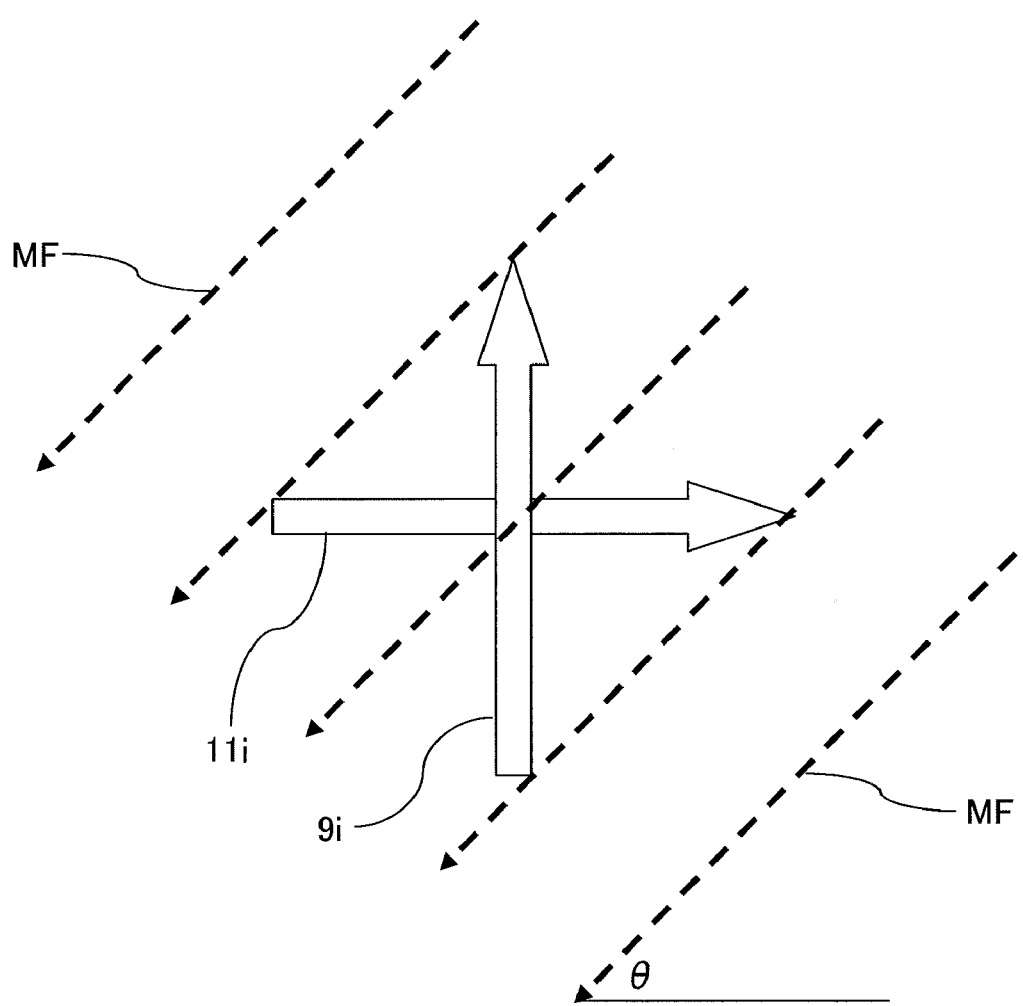
FIG. 2 is a drawing illustrating a direction in which an electric current flows and a direction of a magnetic flux in the eddy current probe in accordance with the present embodiment.

Suppose that an electric current is allowed to flow through the cross coil 7 placed as described above relative to the permanent magnets 3 and 5. As shown in FIG. 2, directions of the electric currents 9i and 11i flowing through the cross coil 7 (the opposing portion 9a of the first coil 9 and the opposing portion 11a of the second coil 11) and the direction of magnetic fluxes MF generated by the permanent magnets intersect with each other.

The following description will discuss an example of tests performed to confirm the effects of the probe 1 in accordance with the present embodiment.

Figure 3A:
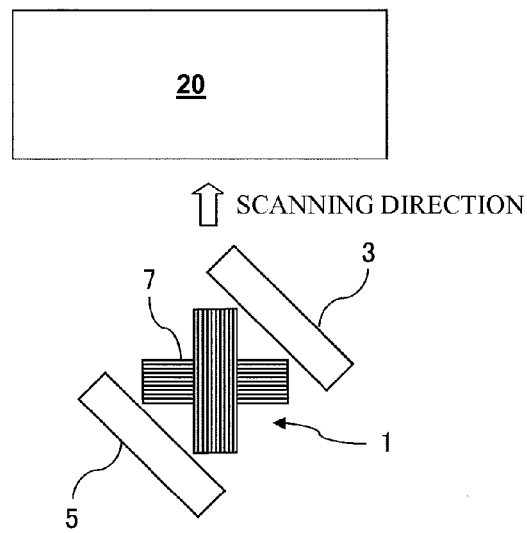
FIG. 3A schematically illustrates an eddy current testing performed by using the eddy current probe in accordance with the present embodiment, and FIG. 3B and FIG. 3C schematically illustrate an eddy current testing performed by using an eddy current probe produced for comparison.
Figure 3B:
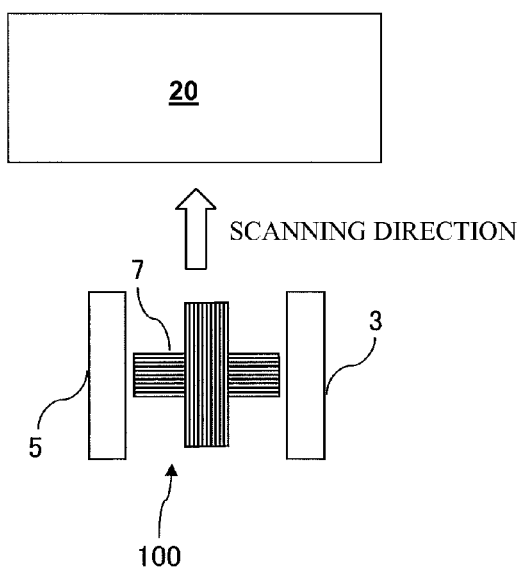
Figure 3C:
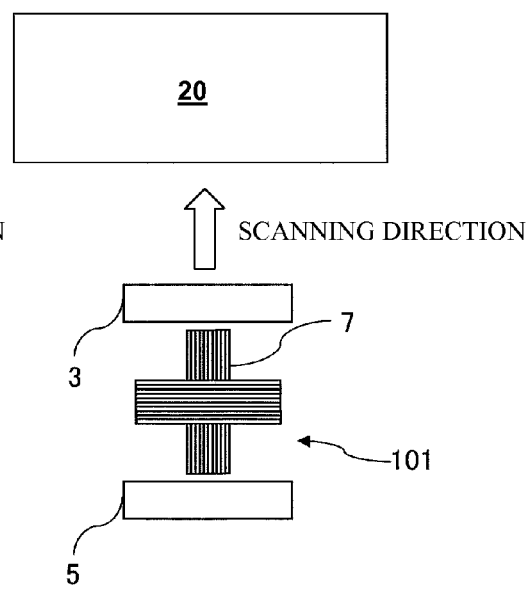

An eddy current testing was performed with the probe 1 of the present embodiment to scan the test object 20 in a direction indicated in FIG. 3A (Examples). For use in comparison, probes 100 and 101 having modes as shown in FIGS. 3B and 3C were prepared, and an eddy current testing was performed with each of the probes 100 and 101 to scan the same test object 20 in a direction shown in FIGS. 3B and 3C (comparative examples). The probe 1 and the probes 100 and 101 had the same specifications except that the direction of the cross coil 7 relative to the permanent magnets 3 and 5 was different. Furthermore, without using the permanent magnets 3 and 5, an eddy current testing was performed by using only the cross coil 7.

The eddy current testing was performed with the probe 1 and the probes 100 and 101 in which permanent magnets 3 and 5 having a plurality of sizes as shown in Table 1 were used, and as electric current frequencies to be applied to the cross coil 7, two kinds of electric current frequencies, that is, 100 kHz and 400 kHz, were used. The voltage of a noise signal detected under each of the above conditions is shown in Table 1.

In comparison with the test result in which only the cross coil 7 is used, the noise signal voltage can be considerably reduced in the probes 100 and 101 provided with the permanent magnets 3 and 5. In the probe 1 of the present embodiment in which the cross coil 7 is placed relative to the permanent magnets 3 and 5 in a way as described above, the noise signal voltage can be further reduced to a half or less in comparison with that of each of the probes 100 and 101.

TABLE 1

| | | Noise signal voltage (Relative value) | | |
| --- | --- | --- | --- | --- |
| | Magnet size (mm) | At 100 kHz | At 400 kHz | 100 kHz/ 400 kHz |
| Comparative Example 1 | 6 × 3 × 6 | 1.0 | 0.4 | 2.75 |
| Comparative Example 2 | | 1.7 | 0.6 | 2.75 |
| Example | | 0.2 | 0.2 | 1.00 |
| Comparative Example 1 | 8 × 2 × 8 | 1.7 | 0.6 | 2.71 |
| Comparative Example 2 | | 1.6 | 0.7 | 0.45 |
| Example | | 0.4 | 0.2 | 1.75 |
| Comparative Example 1 | 10 × 5 × 10 | 0.8 | 0.4 | 2.15 |
| Comparative Example 2 | | 1.2 | 0.5 | 2.60 |
| Example | | 0.3 | 0.2 | 1.83 |
| Comparative Example 1 | 3 × 2 × 3 | 2.7 | 1.1 | 2.44 |
| Comparative Example 2 | | 2.5 | 1.0 | 2.63 |
| Example | | 1.0 | 0.5 | 2.06 |
| Only cross coil | | 3.3 | 1.6 | 2.08 |

Although the reason why noise was remarkably reduced by the use of the probe 1 of the present invention has not been clarified, the following description will discuss the reasons presumed by the present inventors with reference to FIGS. 4A to 4D.

Figure 4A:
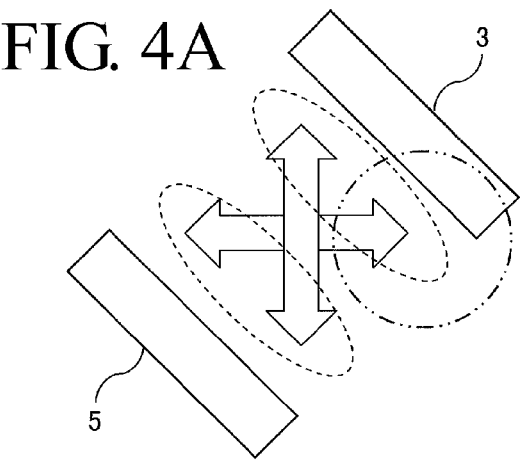
FIGS. 4A to 4D are drawings for explaining effects of the eddy current probe in accordance with the present embodiment.
Figure 4B:
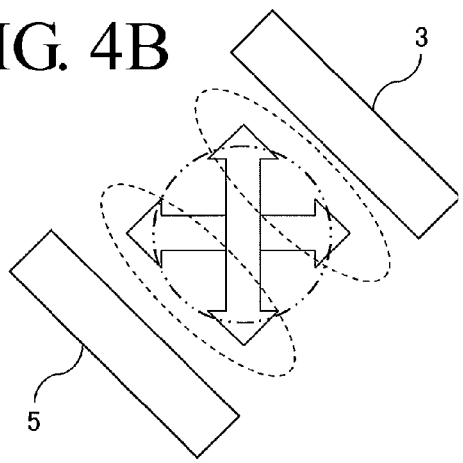
Figure 4C:
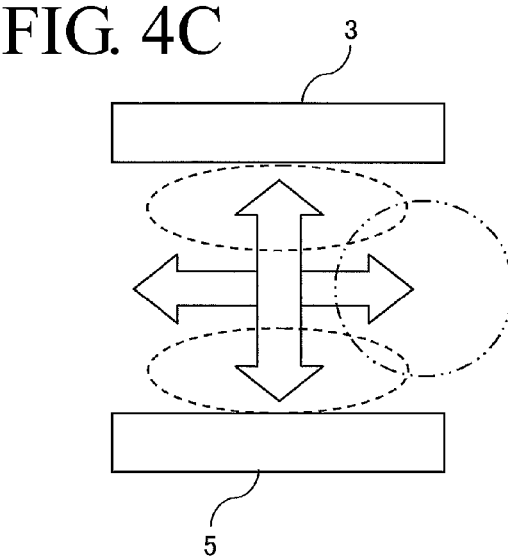

The following consideration is given to a structure in which, as shown in FIGS. 4A and 4C, an area with variations in permeability corresponds to the end portion of the probe 1. As shown in FIG. 4A, in the case of the probe 1 in accordance with the present embodiment, the areas in which an eddy current is generated (a tip portion of an outlined arrow, the same is true hereinafter) and magnetic fields generated by the permanent magnets 3 and 5 overlap in the area with variations in permeability. Therefore, the effect of magnetic saturation becomes greater so that noise due to variations in permeability can be reduced. In contrast, as shown in FIG. 4C, when the probe 1 includes a structure such that an area in which an eddy current is generated does not intersect with magnetic field generated by the permanent magnets 3 and 5, the area with the eddy current being generated and the magnetic field generated by the permanent magnets 3 and 5 do not overlap in the area with variations in permeability. Therefore, the effect of magnetic saturation is small, with the result that the effects of reduction of noise caused by variations in permeability become small.

Figure 4D:
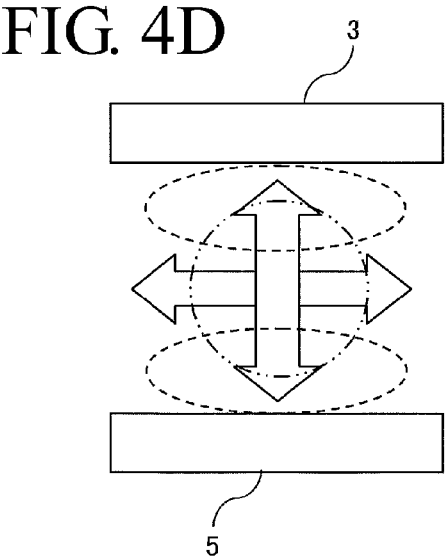

Next, the following consideration is given to a structure in which, as shown in FIGS. 4B and 4D, an area with variations in permeability corresponds to the center of the probe 1. As shown in FIG. 4B, in the case of the probe 1 in accordance with the present embodiment, the magnetic fields generated by the permanent magnets 3 and 5 uniformly act on the area in which an eddy current is generated by the cross coil 7. As a result, the noise can be reduced. In contrast, as shown in FIG. 4D, when the probe 1 includes a structure such that an area in which an eddy current is generated does not intersect with the magnetic field generated by the permanent magnets 3 and 5, no magnetic fields act on the area in which an eddy current in a horizontal direction in the Figure is generated and therefore the effect of magnetic saturation varies depending on the directions, thereby making the noise reduction effect smaller.

Although no limitations are given to the intersecting angle ($\theta$ in FIG. 2), the intersecting angle is preferably set to 30 to 60°, as described earlier, the intersecting angle is more preferably set to 40 to 50°, and the intersecting angle is most preferably set to 45°.

The present embodiment has exemplified a differential coil of a self induction-type as the cross coil 7. However, the present invention may be applied to a differential coil of a mutual induction-type or an absolute coil of a mutual induction-type, as a cross coil.

Figure 5:
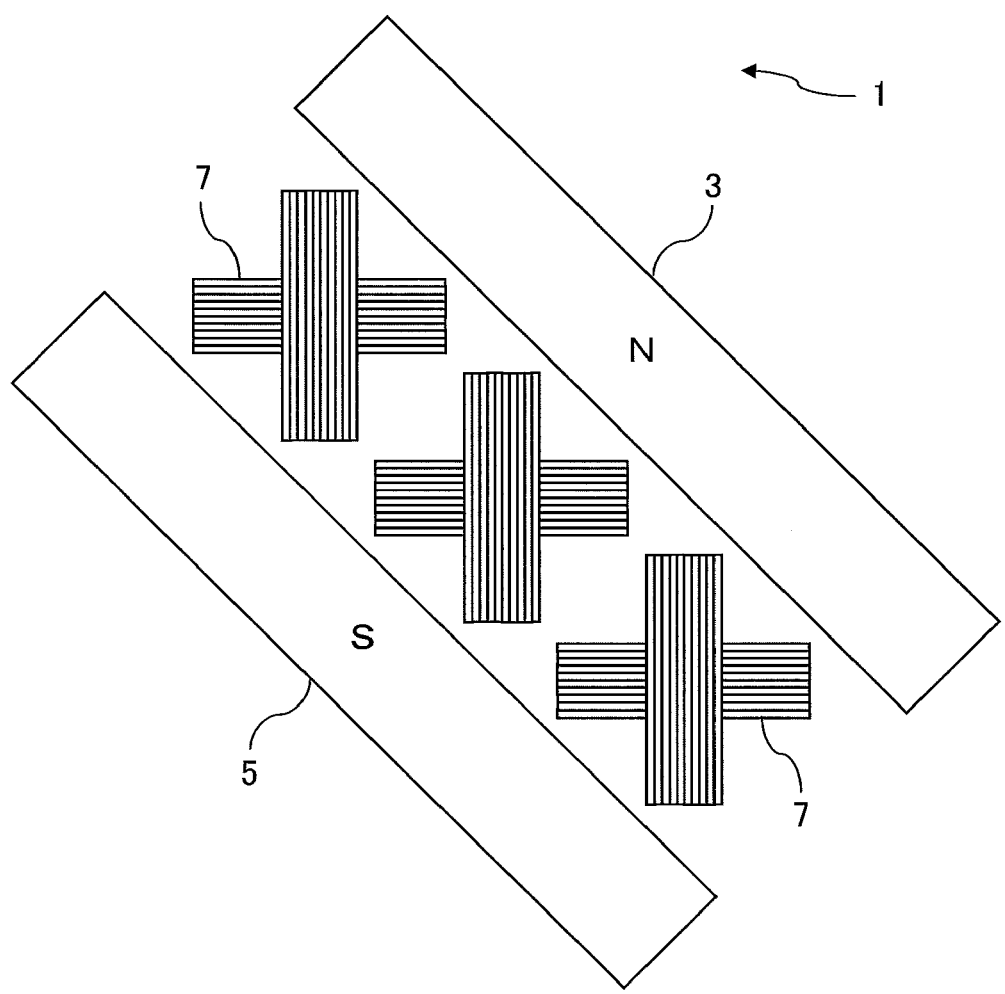
FIG. 5 is a drawing illustrating an example in which the present invention is applied to a multi-coil type probe.

Furthermore, the present embodiment has exemplified a structure in which a single cross coil 7 is placed between the permanent magnets 3 and 5. However, as shown in FIG. 5, the present invention may be applied to a probe of a multi coil type in which a plurality of cross coils 7 are provided between the permanent magnets 3 and 5. Although three cross coils 7 are used in the example of FIG. 5, the number of the cross coils 7 may be arbitrarily set.

Figure 6:
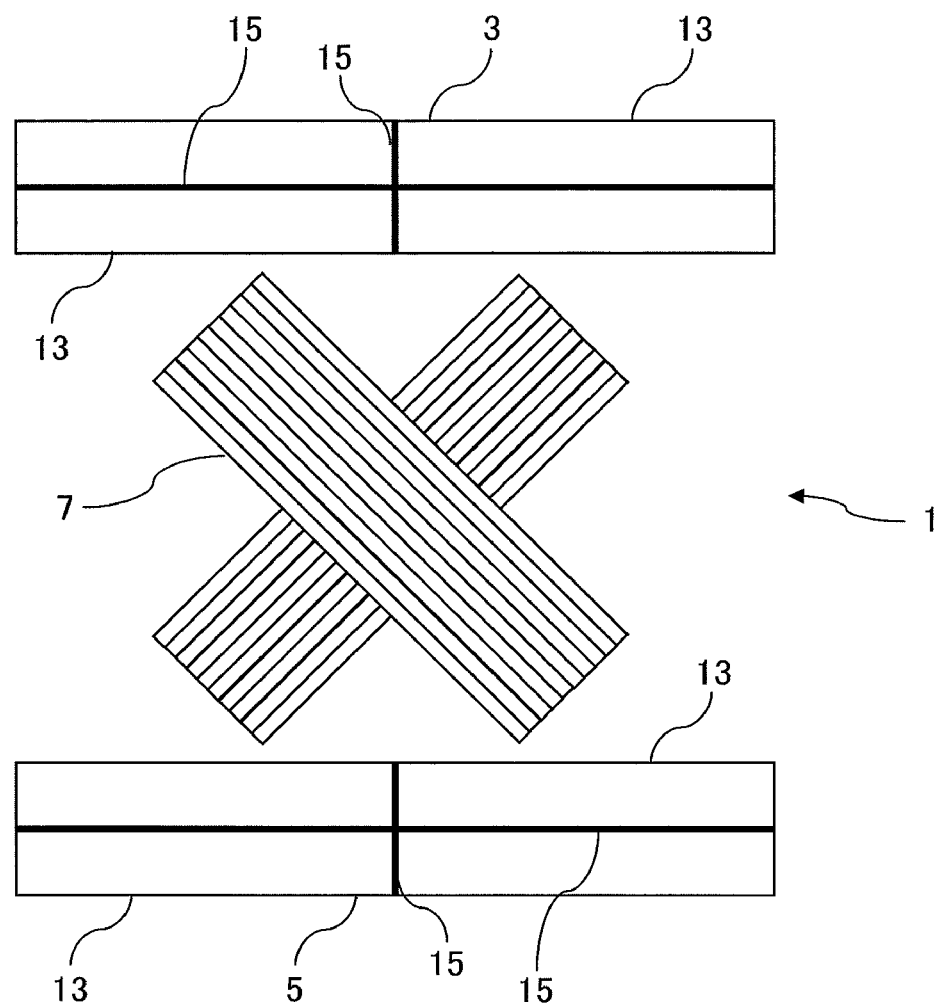
FIG. 6 is a drawing illustrating an example in which a permanent magnet is composed of segment magnets.

Although the present embodiment has exemplified a structure in which the permanent magnets 3 and 5 are formed as an integral unit, the present invention may have a structure in which, as shown in FIG. 6, permanent magnets 3 and 5 may be composed of a plurality of segment magnets 13. In this case, an electric insulating layer 15 is preferably interposed between joining surfaces of the adjacent segment magnets. The advantages of this arrangement are explained as follows: Upon application of an electric current to the cross coil 7, eddy currents are generated on the permanent magnets 3 and 5, with the result that these eddy currents give influences to the results of detection for a defect by the cross coil 7. However, by forming the permanent magnets 3 and 5 using the plural segment magnets 13, with the electric insulating layer 15 being interposed between the joining surfaces, the generation of eddy currents can be suppressed. Therefore, even when the permanent magnets 3 and 5 are provided, it becomes possible to obtain the same detection results as those with no magnets being provided. It is to be noted that the segment magnets 13 may be bonded to each other by using an adhesive agent made of a resin to join the segment magnets 13 to each other with the electric insulating layer 15 interposed between them.

Figure 7A:
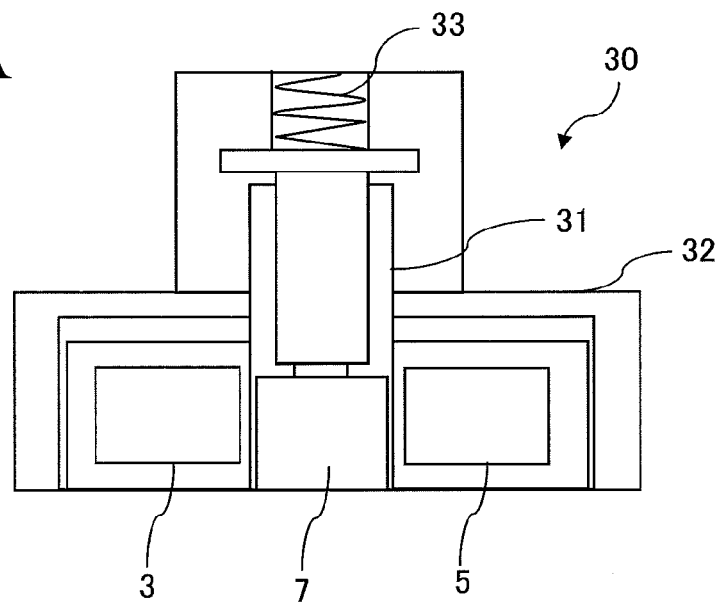
FIG. 7A and FIG. 7B are cross-sectional views illustrating a supporting tool for the eddy current probe in accordance with the present embodiment.
Figure 7B:
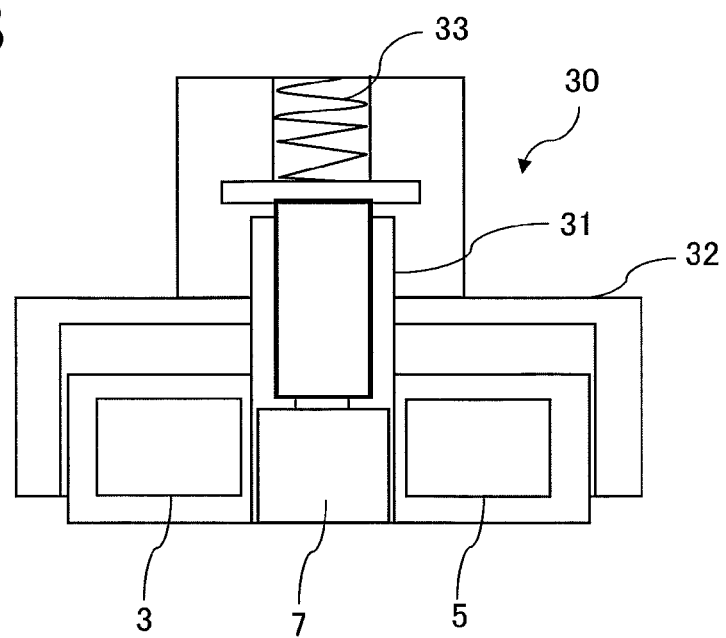

Next, upon actually performing an eddy current testing with the probe 1, a supporting tool 30, for example, as shown in FIGS. 7A and 7B, is preferably used.

As shown in FIGS. 7A and 7B, the supporting tool 30 is provided with a main body 31 that can move up and down integrally with the probe 1, that is, the permanent magnets 3 and 5 and the cross coil 7 without changing the positional relations among the magnets 3 and 5 and the coil 7, a housing 32 that houses the main body 31 and a spring 33 that is connected to the main body 31.

The operator performs an eddy current testing while the supporting tool 30 held by the hand is being moved with respect to a test object. In a case where there are irregularities on the test object, the probe 1 is moved following the irregularities by means of the spring 33. Furthermore, the relative positional relation among the permanent magnets 3 and 5 and the cross coil 7 is unchanged in the probe 1, and thus there is no fear of an electric current being induced in the cross coil 7.

In addition to these, it is needless to say that the invention is not limited to the above embodiments, but that various changes may be made within the scope not departing from the gist of the invention.

What is claimed is:

1. An eddy current probe comprising:
   a permanent magnet that generates a magnetic field in a predetermined direction; and
   a cross coil placed in the magnetic field generated by the permanent magnet,
   wherein the cross coil comprises a first coil and a second coil,
   the first coil and the second coil each comprise opposing portions designed to be opposed in parallel to a test object,
   a first direction is a direction in which the opposing portions of the first coil extend,
   a second direction is a direction in which the opposing portions of the second coil extend,
   a third direction is a direction in which the permanent magnet extends,
   an axial line extending in the first direction intersects an axial line extending in the third direction, and
   an axial line extending in the second direction intersects the axial line extending in the third direction.

2. The eddy current probe according to claim 1, wherein:
   the permanent magnet comprises a pair of permanent magnets, each having a rectangular parallelepiped shape; and
   the cross coil is placed between the pair of permanent magnets.

3. The eddy current probe according to claim 1, wherein the axial line extending in the first direction intersects with the axial line extending in the third direction at an angle in a range from 30 to 60°, and
   the axial line extending in the second direction intersects with the axial line extending in the third direction at an angle in a range from 30 to 60°.

4. The eddy current probe according to claim 1, wherein the axial line extending in the first direction intersects with the axial line extending in the third direction at an angle in a range from 40 to 50°, and the axial line extending in the second direction intersects with the axial line extending in the third direction at an angle in a range from 40 to 50°.

* * * * *